United States Patent
Kanki

(10) Patent No.: US 10,458,968 B2
(45) Date of Patent: Oct. 29, 2019

(54) WATER QUALITY ANALYSIS DEVICE

(71) Applicant: Shimadzu Corporation, Kyoto (JP)

(72) Inventor: Yoshihide Kanki, Otsu (JP)

(73) Assignee: Shimadzu Corporation,
Nishinokyo-Kuwabaracho, Nakagyo-ku,
Kyoto-shi, Kyoto (JP)

( * ) Notice: Subject to any disclaimer, the term of this patent is extended or adjusted under 35 U.S.C. 154(b) by 53 days.

(21) Appl. No.: 15/564,418

(22) PCT Filed: Apr. 10, 2015

(86) PCT No.: PCT/JP2015/061214
§ 371 (c)(1),
(2) Date: Oct. 4, 2017

(87) PCT Pub. No.: WO2016/163024
PCT Pub. Date: Oct. 13, 2016

(65) Prior Publication Data
US 2018/0136186 A1 May 17, 2018

(51) Int. Cl.
*G01N 33/18* (2006.01)
*C02F 1/58* (2006.01)
(Continued)

(52) U.S. Cl.
CPC .............. *G01N 33/18* (2013.01); *C02F 1/58* (2013.01); *C02F 1/72* (2013.01); *G01N 31/005* (2013.01);
(Continued)

(58) Field of Classification Search
CPC .. G01N 33/18; G01N 33/1846; G01N 31/005; G01N 31/227; G01N 1/34;
(Continued)

(56) References Cited

U.S. PATENT DOCUMENTS 4,277,438 A * 7/1981 Ejzak ................... G01N 31/005
250/436
5,567,621 A * 10/1996 Tahara ................... G01N 21/78
436/103
(Continued)

FOREIGN PATENT DOCUMENTS

CN 2782723 Y 5/2006
EP 0634646 B1 1/1999
(Continued)

OTHER PUBLICATIONS

International Search Report for PCT/JP2015/061214, dated Jun. 9, 2015.
(Continued)

*Primary Examiner* — Joseph W Drodge
(74) *Attorney, Agent, or Firm* — Muir Patent Law, PLLC

(57) ABSTRACT

Provided is a water quality analysis device capable of keeping the device in a clean state without leaving an operation at the time of device power supply activation to an operator and without wasting time and wash water. The water quality analysis device is configured such that: a memory 21 capable of storing a stored content in a cut-off state of the device power supply is provided; the states of the vessels, such as an IC reactor 1 and a TC reactor 2, in which sample water is injected at the time of an analysis operation are sequentially stored in the memory 21; contents of the memory 21 are read at the time of the device power supply activation; and a cleaning operation is automatically executed according to prescribed procedures with the states read for each reactor 1 and 2 as a starting point. Thus, even after the power supply interruption due to, e.g., power outage, the device is kept in a clean state with minimum necessary operations.

8 Claims, 2 Drawing Sheets

(51) Int. Cl.
*C02F 1/72* (2006.01)
*G01N 31/00* (2006.01)
*G01N 31/22* (2006.01)
*C02F 101/10* (2006.01)
*C02F 101/16* (2006.01)

(52) U.S. Cl.
CPC ..... *G01N 31/227* (2013.01); *B01D 2257/404* (2013.01); *B01D 2257/55* (2013.01); *C02F 2101/105* (2013.01); *C02F 2101/163* (2013.01); *C02F 2101/166* (2013.01)

(58) Field of Classification Search
CPC ............... G01N 2201/002; G01N 2201/10; C02F 1/58; C02F 1/72; C02F 2101/166; C02F 2101/163; C02F 2101/105; C02F 1/008; C02F 1/62; C02F 1/67; C02F 1/76; C02F 1/83; C02F 1/105; C02F 1/116; C02F 1/129; C02F 1/187; C02F 1/60; C02F 1/608; C02F 1/63; B01D 2257/55; B01D 2257/404; B01D 2257/40; G01J 3/00; G01J 3/12; G01J 3/28; G01J 3/283; B08B 13/00; B01J 19/0033; B01J 19/0006; B01J 19/0046; B01J 2219/0049; B01J 2219/00164; B01J 2219/00166; B01J 2219/00274; B01J 2219/0068; B01J 2219/00686; B01J 2219/00698; B01J 2219/005; B01J 2219/00389; B01J 2219/00391; B01J 2219/00452; B01J 2219/00277; B01J 2219/00351
USPC ....... 210/96.1, 106, 141; 356/300, 319, 326; 422/62, 67, 82.05, 83, 105, 116, 187, 422/600, 608, 630; 436/171, 177; 134/18, 42, 56, 56 R, 115
See application file for complete search history.

(56) References Cited

U.S. PATENT DOCUMENTS

| | | | | |
|---|---|---|---|---|
| 5,629,212 A | * | 5/1997 | Herman | G01N 33/182 204/401 |
| 5,820,823 A | * | 10/1998 | Godec | G01N 27/06 422/78 |
| 2003/0211626 A1 | * | 11/2003 | Davenport | G01N 27/021 436/146 |
| 2003/0223909 A1 | * | 12/2003 | Oberbeck | B01F 5/0604 422/606 |
| 2004/0241865 A1 | * | 12/2004 | Gabski | B01J 19/0093 436/49 |
| 2005/0026273 A1 | * | 2/2005 | Zarur | B01J 19/0046 435/286.1 |
| 2006/0073605 A1 | * | 4/2006 | Horan | G01N 31/005 436/155 |
| 2010/0098588 A1 | * | 4/2010 | Fujiyama | G01N 33/1846 422/82.02 |
| 2010/0193413 A1 | * | 8/2010 | Lendenfeld | C12M 33/14 210/85 |
| 2012/0107947 A1 | * | 5/2012 | Akechi | G01N 33/1846 436/146 |
| 2013/0078617 A1 | * | 3/2013 | Ueda | G01N 35/00623 435/5 |
| 2016/0018376 A1 | * | 1/2016 | Hammerschmidt | G01N 21/3504 436/146 |

FOREIGN PATENT DOCUMENTS

| | | |
|---|---|---|
| JP | 58-60264 | 4/1983 |
| JP | 07027706 A | 1/1995 |
| JP | 2006-047323 A | 2/2006 |
| JP | 2008-032691 A | 2/2008 |
| JP | 2012-225843 A | 11/2012 |
| JP | 2013-019701 A | 1/2013 |

OTHER PUBLICATIONS

Notification of Reasons for Refusal for corresponding application No. CN 201580078424.2, dated Jul. 1, 2019. Submitted with a machine translation.

* cited by examiner

WATER QUALITY ANALYSIS DEVICE

TECHNICAL FIELD

The present invention relates to a water quality analysis device for analyzing a concentration of total organic carbon, total nitrogen, total phosphorus, etc., in industrial waste water or environmental water such as rivers and lakes.

BACKGROUND ART

In a water quality analysis device for analyzing a concentration of a specific component in sample water, in generally, a concentration of an analysis target component in sample water is obtained by injecting sample water into a reactor to cause a reaction corresponding to the analysis target component, sending a specific gas generated with this to a gas detection unit, and measuring its gas concentration, alternatively, by generating a specific ion in sample water by a reaction in a reactor, injecting the sample water after the reaction into a measuring cell of an absorption spectrometer, and measuring the ion concentration (see, for example, Patent Document 1).

In such an analysis device, usually, after completion of one analysis, wash water (generally pure water used as dilution water) is injected into a vessel such as a reactor or a measuring cell into which sample water is injected, and discharged under prescribed procedures to automatically clean the inside of the vessel so that the previous sample water does not affect the subsequent analysis (see, for example, Patent Document 2).

PRIOR ART

Patent Document

Patent Document 1: Japanese Unexamined Patent Application Publication No. 2013-019701
Patent Document 2: Japanese Unexamined Patent Application Publication No. 2012-225843

SUMMARY OF THE INVENTION

Problems to be Solved by the Invention

By the way, in a water quality analysis device having a cleaning function as described above, when the device power supply is unexpectedly interrupted such as an unexpected power outage, since the device cannot detect in what state the power supply was interrupted, it is necessary to perform one of the followings at the next power supply initiation.

<1> By taking safety measures, at the time of the power supply activation, a cleaning operation is carried out in a series of procedures from the beginning of a cleaning operation, that is, the liquid in each vessel is discharged and then wash water is injected and discharged.

<2> An operator determines whether or not a cleaning operation is to be carried out.

In cases where a series of cleaning operations starting from the discharge in the vessel are always carried out at the time of the power supply initiation as described in <1>, it takes time to execute a series of cleaning operations from the activation of the device power supply until the initiation of the actual analysis, and a considerable amount of wash water (pure water) is required. Further, even in cases where the device power supply is interrupted in a state in which the analysis and the subsequent washing were completed normally, a cleaning operation will be executed again at the time of the device power supply activation, so there arises a problem that time and wash water will be wasted.

On the other hand, as described in <2>, in cases where it is determined whether or not the cleaning operation is to be carried out based on the operator's decision, it is necessary for the operator to recognize that the power outage was occurred and the decision should be made after checking the internal state. Therefore, it is inconvenient for the operator and the burden increases.

The present invention was made in view of the aforementioned circumstances, and aims to provide a water quality analysis device capable of always starting an analysis operation in the shortest time without leaving an operation at the time of a device power source activation to an operator and eliminating an influence of a previous analysis without wasting time and wash water.

Means for Solving the Problems

In order to solve the aforementioned problems, a water quality analysis device according to the present invention is a device configured to analyze a concentration of a specific component contained in sample water, includes: at least one reactor configured to cause a reaction for the sample water injected through liquid feeding means corresponding to an analysis target component, wherein a concentration of the analysis target component in the sample water is obtained by performing a measurement by introducing a gas containing the analysis target component generated by the reaction in the reactor to a gas detection unit or by injecting the sample water after the reaction in the reactor into a measuring cell through the liquid feeding means; control means configured to control a cleaning operation for individually cleaning the reactor and the measuring cell under predetermined procedures including operations of discharging analyzed sample water from the reactor or the measuring cell and injecting/discharging wash water into/from the reactor or the measuring cell through the liquid feeding means; and a memory configured to retain a stored content even when a device power supply is interrupted, wherein the memory individually stores states of the reactor and the measuring cell, and wherein the control means reads stored contents of the memory at the time of device power supply activation, and the reactor and the measuring cell are individually cleaned under the procedures with a state based on the stored contents as a starting point.

A more specific configuration of the present invention may be exemplified by a configuration in which the device further includes an IC reactor configured to convert inorganic carbon in the sample water into carbon dioxide gas, and a TC reactor configured to convert total carbon in the sample water into carbon dioxide, wherein each of the reactors is a target for a state storage by the memory and a cleaning operation by the control unit.

As another specific configuration of the present invention, the following configuration may be exemplified. The device further includes a reactor configured to convert a nitrogen compound and/or a phosphorus compound in the sample water into a nitrate ion or a phosphate ion, and an absorption spectrometer configured to measure a concentration of the nitrate ion or the phosphate ion in the sample water after conversion, wherein a measuring cell of the absorption spectrometer and the reactor are targets for a state storage by the memory and a cleaning operation by the control unit.

In the aforementioned configuration, in cases where a preprocessing unit for removing suspended substances in the sample water is provided at a front stage of the reactor, the preprocessing unit is also made as a target for a state storage by the state memory by the memory and a cleaning operation by the control unit.

The present invention is to solve the problem by providing a memory capable of retaining a stored content even when the power is interrupted and the state of a reactor or a measuring cell at the time of the power interruption is stored in the memory, and at the time of the device power supply activation, a cleaning operation is started with a state based on the stored contents as a starting point.

In other words, by sequentially storing a state in a vessel such as a reactor, a measuring cell, etc., into which sample water is injected in a nonvolatile memory, etc., the state of each vessel at the time of the device power supply interruption will be stored in the memory. At the time of the next power supply activation, the cleaning operation is automatically executed under a series of procedures with the state stored in the memory as a starting point, so that waste of time and wash water can be avoided.

In the present invention, the target for the storage of the state and the cleaning is a reactor or a measuring cell which serves as an injection vessel of sample water in the device. For example, in an analysis of a TOC meter or the like used for analyzing total carbon, an IC (inorganic carbon) reactor and a TC (total carbon) reactor are the target devices.

On the other hand, in an analysis device such as a TN/TP meter for analyzing total nitrogen and total phosphorus in sample water, the target for the state storage and the cleaning is a reactor that converts nitrogen in the sample water into nitrate ions and also converts phosphorus into phosphate ions and a measuring cell of an absorption spectrometer for measuring the concentration of these ions. In cases where a preprocessing unit for removing suspended substances in the sample water is installed at a front stage of the reactor, this preprocessing unit is also included in the target.

EFFECTS OF THE INVENTION

According to the present invention, even if unexpected device power supply interruption such as power outage occurs, the states of the reactor and the measuring cell at the interruption point are stored, and at the time of the next power supply activation, the device automatically determines whether or not the cleaning operation is to be executed with the stored state as a starting point or whether cleaning is unnecessary. Therefore, the judgment of an operator becomes unnecessary and the processing at the time of the power supply activation can be minimized. Further, waste of time and wash water can be avoided.

EMBODIMENTS FOR CARRYING OUT THE INVENTION

Hereinafter, an embodiment in which the present invention is applied to a TOC meter will be described with reference to FIG. 1. The basic structure of the TOC meter in FIG. 1 is equivalent to that of a conventional one, and the detailed description of portions which are less related to the present invention will be omitted, and the main portions will be described.

Figure 1:
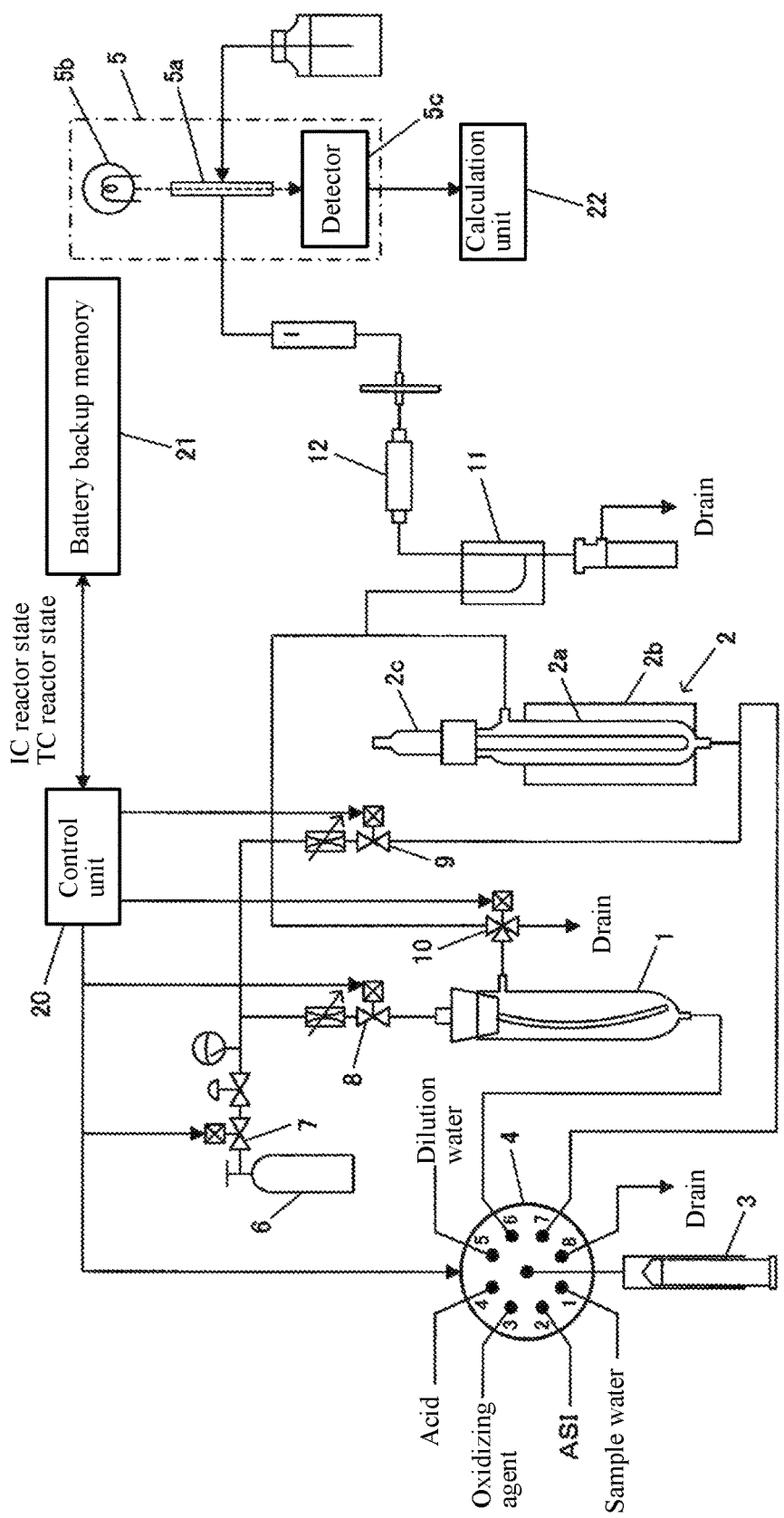
FIG. 1 is a configuration diagram showing an embodiment of the present invention.

The device shown in FIG. 1 is composed of, as main components, an IC reactor 1 which causes a reaction to convert inorganic carbon in sample water into carbon dioxide, a TC reactor 2 which causes a reaction to convert total carbon in sample water into carbon dioxide, a liquid supply system mainly composed of a syringe 3 and an 8-port valve 4 which are used for supplying sample water and dilution water (wash water) or chemicals to the IC reactor 1 and the TC reactor 2, a gas detection unit 5 for detecting carbon dioxide gases generated in each of the reactors 1 and 2, a gas supply system which delivers the gas in each of the reactors 1 and 2 to the gas detection unit 5 by a carrier gas.

Sample water is supplied to one port of the 8-port valve 4, and dilution water (pure water) which also serves as wash water, a reagent such as acid required for the reaction are supplied to other ports. The 8-port valve 4 includes a port connected to a drain. Furthermore, other ports of the 8-port valve 4 are each connected to a liquid inlet/outlet provided at the respective lower ends of the IC reactor 1 and the TC reactor 2, and the common port is connected to the syringe 3. In cases where sample water is sampled by an autosampler, the sample water is supplied to a port connected to an injection port (ASI) of the autosampler.

A carrier gas supplied from a carrier gas inlet 6 is introduced into the IC reactor 1 and the TC reactor 2 via electromagnetic valves 8 and 9 via an electromagnetic valve 7, and the gas in each reactor 1 and 2 are sent to the gas detection unit 5 by the carrier gas. Here, as to the carbon dioxide gas generated in the IC reactor 1, whether to send to the gas detection unit 5 as described above or to discharge to the outside through the drain is selected by the electromagnetic valve 10. The carrier gas introduced into the IC reactor 1 is also used as a gas for sparge (aeration treatment).

The gas detection unit 5 is for detecting a carbonic acid gas, and mainly includes a sample cell 5a configured to hold a gas delivered from the IC reactor 1 or the TC reactor 2, a light source 5b for irradiating infrared ray toward the gas in the sample cell 5a, and the detector 5c for detecting the transmitted light. The output of the detector 5c which is a detection output of the carbon dioxide gas is taken into the calculation unit 22. A dehumidification electronic cooler 11, a halogen scrubber 12, and the like are provided on the upstream side of the sample cell 5a, so that the influence of moisture and halogen gas does not affect detection results.

The syringe 3 and the 8-port valve 4 which are actuators of the liquid supply system and the electromagnetic valves 7, 8, 9, and 10, etc., of the gas supply system are controlled by a drive signal supplied from a control unit 20.

A battery backup memory 21 is connected to the control unit 20, and the states of the IC reactor 1 and the TC reactor 2 are sequentially and individually stored in the battery backup memory 21 based on the control operation by the control unit 20 shown below.

Next, the operation of an embodiment of the present invention having the aforementioned configuration will be described.

In the analysis operation, the 8-port valve 4 and the syringe 3 are driven to inject a small amount of acid together with sample water into the IC reactor 1, and aeration treatment is carried out by introducing sparge gas, whereby the carbon dioxide gas is discharged from the drain through the electromagnetic valve 10 while converting inorganic carbon in the sample water into carbon dioxide gas. With this, after eliminating the inorganic carbon in the sample water, the 8-port valve 4 and the syringe 3 are driven to inject the sample water in the IC reactor 1 into the TC reactor 2.

The TC reactor 2 is configured to cause a reaction to convert total carbon in sample water into carbon dioxide gas by driving the TC combustion tube 2a, the heating furnace 2b, and the UV lamp 2c. The carbon dioxide gas generated here is delivered into the sample cell 5a of the gas detection unit 5 via the dehumidification electronic cooler 11 and the halogen scrubber 12 by introducing carrier gas into the TC reactor 2 and served for detection. This detection result is information corresponding to the amount of total carbon contained in the sample water from which inorganic carbon has already been eliminated, that is, information corresponding to the amount of organic carbon. Thus, the amount of organic carbon in the sample water is obtained by the calculation unit 22.

In the aforementioned operation, the carbon dioxide gas obtained by converting the inorganic carbon in the IC reactor 1 is discharged from the drain to the outside, however, the carbon dioxide gas may be introduced into the gas detection unit 5 by switching the electromagnetic valve 10 and the concentration of inorganic carbon may be determined from the detection result. In that case, sample water is separately injected into the TC reactor 2, and total carbon in the sample water is converted into a carbon dioxide gas and introduced into the gas detection unit 5. The actual total carbon concentration is calculated from the detection result, and the organic carbon concentration is obtained by subtracting the aforementioned inorganic carbon concentration from the calculation result.

In the cleaning operation, for the IC reactor 1 and the TC reactor 2, after draining the sample water remained therein, wash water (dilution water) is injected into each of them, and then the wash water is drained. The drainage of the inside of each of the reactor 1 and 2 is carried out as follows. The 8-port valve 4 is driven to connect corresponding reactor and syringe 3, and in its connected state, the syringe 3 is driven to suck the water in the reactor. Then, the 8-port valve 4 is again driven to connect the syringe 3 and the drain port, and in its connected state, the syringe 3 is driven to discharge the water in the reactor. Injection of wash water into each reactor 1 and 2 is the same as injection of sample water. That is, wash water is sucked with the syringe 3, and then the wash water in the syringe 3 is discharged and injected into the reactor in a state in which the syringe 3 and corresponding reactor are connected by driving the 8-port valve 4.

The battery backup memory 21 successively updates and stores the states in the IC reactor 1 and the TC reactor 2 in accordance with the progress of the analysis and the cleaning operation by the control unit 20. Specific examples are exemplified as follows.

(1) "Sample water is present" indicating a state in which sample water has been injected into the reactor (2) "Sample contamination, Empty" indicating a state in which sample water in the reactor has been discharged (3) "Wash water is present" indicating a state in which wash water has been injected to wash the inside of the reactor (4) "Clean, Empty" indicating a state in which wash water in the reactor has been discharged In the battery backup memory 21, the aforementioned states of respective reactors 1 and 2 are sequentially rewritten depending on the operation state of the device. Therefore, when the device power supply is interrupted, the state of each of the reactors 1 and 2 at the interruption point will be stored.

At the next power supply activation, the control unit 20 reads the stored contents of the battery backup memory 21 and performs the following operations for each of the IC reactor 1 and the TC reactor 2 according to the aforementioned states (1) to (4).

(1) "Sample water is present"→After discharging the sample water, wash water is injected and discharged (2) "Sample contamination, Empty"→Wash water is injected and discharged (3) "Wash water is present"→Wash water is discharged (4) "Clean, Empty"→No action is performed With the above operations, even if there is an unintended interruption of the device power supply such as power outage, the device can be kept in a clean state by the minimum necessary operations without requiring the operator's judgment, and the waste of time and wash water (pure water) can be eliminated.

The aforementioned embodiment shows an example in which the present invention is applied to a TOC meter. However, the present invention can also be applied to a water quality analysis device for analyzing other components. In short, the feature of the present invention resides in that in a vessel in a device into which sample water is injected, the state at the time of the device power supply interruption is stored, and processing according to the stored contents is automatically executed at the time of power supply activation to make each vessel in a clean state.

Figure 2:
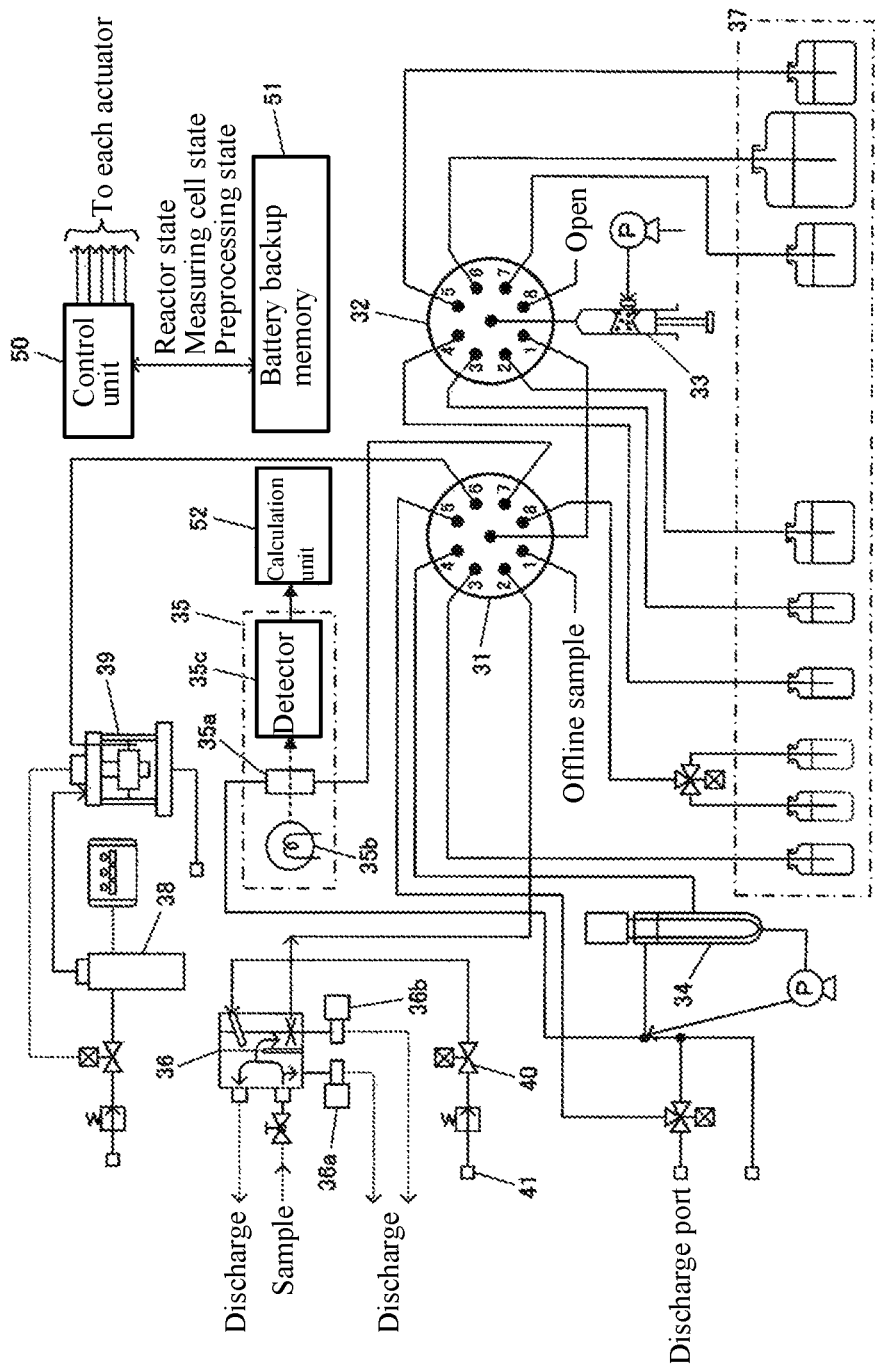
FIG. 2 is a configuration diagram showing another embodiment of the present invention.

Next, FIG. 2 shows an example in which the present invention is applied to a TN/TP meter. The basic configuration of the TN/TP meter in this example is well-known, and is mainly composed of a liquid supply system mainly including two 8-port valves 31 and 32 and a syringe 33, a reactor 34 into which sample water, various reagents, and dilution water are injected by the liquid supply system, and an absorption spectrometer 35 equipped with a measuring cell 35a into which sample water reacted in the reactor 34 is injected.

Sample water is injected into the preprocessing unit 36 and suspended substances and the like are removed. Thereafter, the sample water is sucked into a syringe 33 via 8-port valves 31 and 32. The sucked sample water is injected into the reactor 34 via the 8-port valves 32 and 31. It is configured such that any one of reagents among the reagent group 37 can be selectively injected into the reactor 34 by the liquid supply system. Also to the reactor 34, the dilution water purified by the dilution water purifier 38 and stored in the dilution water source 39 can be injected through the 8-port valve 32 and the 8-port valve 31 after being sucked into the syringe 33 via the 8-port valve 31 and the 8-port valve 32.

The reactor 34 has a heating function and an ultraviolet irradiation function and converts nitrogen in sample water into nitrate ions or phosphorus into phosphate ions by causing a reaction according to a total nitrogen measurement or a total phosphorus measurement.

That is, at the time of a total nitrogen measurement, an alkaline peroxodisulfate potassium solution is added to sample water and ultraviolet irradiation or heating is performed to convert nitrogen in sample water into nitrate ions. Also, at the time of a total phosphorus measurement, neutral peroxodisulfate potassium solution is added to sample water and ultraviolet irradiation or heating is performed to convert phosphorus in the sample water into phosphate ions, and further ammonium molybdate solution and an L-ascorbic acid solution are added as coloring agents to develop color.

In the reactor 34, the sample water after reaction is adjusted in pH by adding a reagent, and then sucked by the syringe 33 via the 8-port valve 31 and the 8-port valve 32 and injected from the syringe 33 via the 8-port valve 32 and the 8-port valve 31 into the measuring cell 35a of the absorption spectrometer 35. The absorption spectrometer 35 has a structure in which a light source 35b and a detector 35c are disposed on both sides of the measuring cell 35a. At the time of measuring total nitrogen, ultraviolet light having a wavelength of 220 nm corresponding to the light absorption characteristics by nitrate ions is irradiated to the sample water in the measuring cell 35a, and the detection result by the detector 35c is taken into a calculation unit 52 as nitrate ion concentration information, so that the total nitrogen concentration in the sample water is calculated. Further, at the time of measuring total phosphorus, the absorbance of the phosphate ion colored in the sample water is measured by irradiating light having a wavelength of, for example, 880 nm to the measuring cell 35a. Based on the result, the total phosphorus concentration in the sample water is calculated in the calculation unit 52.

The sample water subjected to the absorbance measurement as described above will be discharged from the measuring cell 35a to the outside of the device by the aforementioned liquid supply system.

Regarding the cleaning operations of the reactor 34 and the measuring cell 35a, after discharging the sample water remained therein, the dilution water in the dilution water source 39 is injected as wash water into the insides of the reactor 34 and the measuring cell 35a by the aforementioned liquid supply system and then the wash water is discharged to the outside by the liquid supply system.

Further, regarding the cleaning operation of the preprocessing unit 36, pinch valves 36a and 36b are opened to discharge the sample water in the unit to the outside, and then the electromagnetic valve 40 is opened to inject tap water from a tap water inlet 41 into the preprocessing unit 36, and the pinch valves 36a and 36b are opened to discharge the tap water to the outside.

Each actuator such as the 8-port valves 31 and 32, the syringe 33, the electromagnetic valve 40, etc., which operates in the aforementioned cleaning operation and analysis operation is controlled by a drive signal from the control unit 50. A battery backup memory 51 is connected to the control unit 50, and the states of the reactor 34, the measuring cell 35a, and the preprocessing unit 36 are sequentially and individually updated and stored in the battery backup memory 51 in the same manner as in the previously described embodiment. Specifically, in the same manner as in the previously described embodiment, the states include (1) "Sample water is present", (2) "Sample contamination, Empty", (3) "Wash water is present", and (4) "Clean, Empty".

Also in this embodiment, at the time of the power supply activation, the control unit 50 reads the stored contents of the battery backup memory 51. Depending on the aforementioned conditions of the reactor 34, the measuring cell 35a, and the preprocessing unit 36, if the state is (1) "Sample water is present", after discharging the sample water, wash water (tap water in the preprocessing unit 36, hereinafter the same) is injected and discharged, if the state is (2) "Sample contamination, Empty", wash water is injected and discharged, and if the state is (3) "Wash water present", the wash water is discharged. Further, if the state is (4) "Clean, Empty", no action is executed.

With the aforementioned operations, in the same manner as in the aforementioned embodiment, even if an unintended interruption of the device power supply such as power outage occurs, the device can be kept in a clean state by minimum necessary operations without requiring the operator's judgment, and waste of time and wash water (pure water) can be eliminated.

Here, in the embodiment of FIG. 1, in cases where sample water is sampled by an autosampler, sample water is supplied through the port of the 8-port valve 4 connected to the discharge port (ASI) of the autosampler as described above. In the autosampler, however, a preprocessing unit 36 having the same cleaning function as that shown in FIG. 2 is provided, and regarding the preprocessing unit thereof, the states are sequentially stored in a battery backup memory in the same manner as in the embodiment shown in FIG. 2. At the time of device power activation, the stored content is read and, in the same manner as in the embodiment shown in FIG. 2, a cleaning operation corresponding to the stored content is executed.

In the aforementioned embodiments, examples in which the present invention is applied to the TOC meter and the TN/TP meter have been described, but it should be noted that the present invention is not limited to them and other combinations may be allowed. In short, regarding the reactor or the measuring cell in which sample water is injected during the analysis operation, or the preprocessing unit in a water quality analysis device, its state is stored in the battery backup memory or the like, and at the time of the device power supply activation, the apparatus is made to a clean state by necessary minimum operations depending on the state stored in the memory.

In the present invention, it is a matter of course that as the memory for storing the stored content at the time of the device power supply interruption, other than a battery backup memory, a nonvolatile memory or the like may be used.

DESCRIPTION OF REFERENCE SYMBOLS

1: IC reactor
2: TC reactor
3: syringe
4: 8-port valve
5: gas detection unit
6: carrier gas inlet
7, 8, 9, 10: electromagnetic valve
11: dehumidification electronic cooler
12: halogen scrubber
20: control unit
21: battery backup memory
22: calculation unit
31, 32: 8-port valve
33: syringe
34: reactor
35: absorption spectrometer
35a: measuring cell
36: preprocessing unit
37: reagent group
38: dilution water purifier
39: dilution water source
40: electromagnetic valve
41 tap water inlet

The invention claimed is:
1. A water quality analysis device configured to analyze a concentration of at least one analysis target component contained in sample water, comprising:

at least one reactor configured to cause a reaction corresponding to an analysis target component in the sample;

a measuring cell for the analyzing of the concentration of least one analysis target of the sample water, wherein the concentration of the at least one analysis target component is obtained by performing at least one measurement with the measuring cell, the at least one measurement is chosen from the group consisting of: introducing a gas containing the at least one analysis target component generated by the reaction in the at least one reactor to a gas detection unit comprising the measuring cell and injecting the sample water into the measuring cell after the reaction in the at least one reactor;

control means configured to control a cleaning operation for individually cleaning the at least one reactor and the measuring cell according to at least one predetermined procedure, the at least one predetermined procedure selected from discharging analyzed sample water from the at least one reactor and/or the measuring cell, injecting wash water into the at least one reactor and/or the measuring cell, and discharging wash water from the at least one reactor and/or the measuring cell; and a memory that is configured to retain stored content, the stored content being retained by the memory in the event of power loss to the memory, wherein:

the memory stored content includes operation states of the at least one reactor and of the measuring cell as the stored content, the control means is configured to read the stored content of the memory upon power activation, and the at least one predetermined procedure includes a starting point that is based on the stored content of the memory.

2. The water quality analysis device as recited in claim 1, wherein the at least one reactor comprises:

an IC reactor configured to convert inorganic carbon in the sample water into carbon dioxide gas; and a TC reactor configured to convert total carbon in the sample water into carbon dioxide, wherein:

the operation states of the at least one reactor stored by the memory include an operation state of the IC reactor and an operation state of the TC reactor, and the cleaning operation includes cleaning of the IC reactor and cleaning of the TC reactor.

3. The water quality analysis device as recited in claim 1, wherein the measuring cell comprises:

an absorption spectrometer, wherein:

the at least one reactor is configured to convert a nitrogen compound and/or a phosphorus compound in the sample water into a nitrate ion or a phosphate ion, the absorption spectrometer is configured to measure a concentration of the nitrate ion and/or a concentration of the phosphate ion in the sample water after conversion, the memory is further configured to individually store operation states of the absorption spectrometer, and the cleaning operation includes cleaning of the absorption spectrometer.

4. The water quality analysis device as recited in claim 1, further comprising:

a preprocessing unit that is provided at a front stage of the at least one reactor, the preprocessing unit being configured to remove a suspended substance in the sample water, wherein:

the memory is further configured to individually store operation states of the preprocessing unit in the stored content, and the cleaning operation includes cleaning of the preprocessing unit.

5. A method for analyzing a concentration of at least one analysis target component contained in sample water, comprising:

providing at least one reactor and a measuring cell;

causing a reaction in the at least one reactor that corresponds to an analysis target component in the sample water;

performing at least one measurement to obtain the concentration of the at least one analysis target component;

controlling at least one cleaning operation on the basis of at least one predetermined procedure;

retaining stored content in a memory, the stored content being retained by the memory in the event of power loss to the memory; and reading the stored content of the memory upon power activation, wherein:

retaining the stored content in the memory includes individually storing operation states of the at least one reactor and operation states of the measuring cell, the at least one predetermined procedure includes a starting point that is based on the stored content, and controlling at least one cleaning operation selected from discharging analyzed sample water, injecting wash water, and discharging the wash water.

6. The method for analyzing a concentration of at least one analysis target component contained in sample water according to claim 5, further comprising:

converting inorganic carbon in the sample water into carbon dioxide gas; and converting total carbon in the sample water into carbon dioxide, wherein:

the at least one reactor comprises an IC reactor configured to convert inorganic carbon in the sample water into carbon dioxide gas; and a TC reactor configured to convert total carbon in the sample water into carbon dioxide, and controlling the at least one cleaning operation further includes cleaning of the IC reactor and cleaning of the TC reactor.

7. The method for analyzing a concentration of at least one analysis target component contained in sample water according to claim 5, further comprising:

converting a nitrogen compound and/or a phosphorus compound in the sample water into a nitrate ion or a phosphate ion in the at least one reactor; and measuring a concentration of the nitrate ion and/or a concentration of the phosphate ion with an absorption spectrometer comprised in the measuring cell, wherein:

retaining stored content in the memory further includes individually storing operation states of the absorption spectrometer, and controlling the at least one cleaning operation further includes cleaning of the absorption spectrometer.

8. The method for analyzing a concentration of at least one analysis target component contained in sample water according to claim 7, further comprising removing a suspended substance in the sample water.

* * * * *